United States Patent [19] [11] Patent Number: 4,843,003
Henikoff et al. [45] Date of Patent: Jun. 27, 1989

[54] PROCESS FOR PRODUCING SHORTENED TARGET DNA FRAGMENTS USABLE IN SEQUENCING LARGE DNA SEGMENTS

[75] Inventors: Steven Henikoff; Richard E. Gelinas, both of Seattle, Wash.

[73] Assignee: Fred Hutchinson Cancer Research Center, Seattle, Wash.

[21] Appl. No.: 581,311

[22] Filed: Feb. 17, 1984

[51] Int. Cl.$^4$ .................. C12P 19/32; C12N 15/00; C07H 15/12

[52] U.S. Cl. .............................. 435/91; 435/172.3; 435/6; 536/27; 935/1; 935/22; 935/77

[58] Field of Search ............... 435/91, 68, 172.3, 317, 435/6; 935/9, 76, 77, 22

[56] References Cited

OTHER PUBLICATIONS

Rogers et al, "Exonuclease III of *Eacherichia coli*, K 12, an AP Endonuclease," *Methods in Enzymology*, vol. 6S, (1976), pp. 201–211.

Guo et al, "New Rapid Methods for DNA Sequencing Based on Exonuclease III Digestion Followed by Repair Synthesis", *Nucleic Acid Research*, V. 10, (1982), pp. 2065–2084.

Guo et al, "An Improved Strategy for Rapid Direct Sequencing of Both Strands of Long DNA Molecules Cloned in a Plasmid", *Nucleic Acids Research*, V. 11, (1983), pp. 5521–5540.

Henikoff, "Unidirectional Digestion with Exonuclease (List continued on next page.)

*Primary Examiner*—Thomas G. Wiseman
*Assistant Examiner*—Thomas D. Mays
*Attorney, Agent, or Firm*—Christensen, O'Connor, Johnson & Kindness

[57] ABSTRACT

A process is provided for producing an ordered series of cloned, circular, DNA molecules containing shortened target DNA segments derived from a long target DNA segment, which are suitable for use in determining the nucleotide sequence of the long target DNA segment, or for targeting specific regions within the target DNA segment. The process includes producing, by molecular cloning, a plurality of double-stranded recombinant DNA molecules each containing: (i) vector DNA; (ii) a sequencing primer binding site; and, (iii) a DNA region having unique endonuclease sites and a long target DNA segment. The sequencing primer binding site is spaced from the long target DNA segment by at least a portion of said DNA region having the unique endonuclease sites. The plurality of double-stranded circular recombinant DNA molecules are cleared using two restriction endonucleases. The cleavage occurs in the portion of the DNA having unique endonuclease sites lying between the long target DNA segment and the sequencing primer binding site. The cleavage and, if necessary, subsequent processing steps, produces double-stranded linear DNA molecules having an end containing a long target DNa segment that is susceptible to exonuclease digestion and a sequencing primer binding site end that is not susceptible to exonuclease digestion. Next, the target DNA segment end is subjected to exonuclease digestion. At timed intervals, portions of the exonuclease digested linear double-stranded DNA molecules are removed. Since part of the target DNA segment has been deleted by the exonuclease, the removed linear double-stranded DNA molecules include shortened target DNA segments. Next, the removed linear double-stranded DNA molecules are blunted and then recirculated to reform circular recombinant DNA molecules. The reformed recombinant DNA molecules are cloned to produce a plurality of circular DNA molecules containing shortened target DNA segments that differ in length by the amount of target DNA that was removed by the exonuclease. The reformed circular DNA molecules are suitable for use in DNA sequencing other molecular manipulations of genetic material.

33 Claims, 6 Drawing Sheets

OTHER PUBLICATIONS

III Creates Targetted Breakpoints for DNA Sequencing", *Gene*, V. 28, (1984), pp. 351–359.

Putney et al, "A DNA Fragment with an Alpha-Phosphosothroate Nucleotide at One End is Asymmetrically Blocked from Digestion by Exonuclease III and Can be Replocated in-vivo", *Proc. Natl. Acad. Sci.*, V. 75, (1981), p. 7350.

Roberts et al., *Meth. in Enzymol.*, vol. 68, pp. 473–482, 1979.

Zinder et al, 1982, "The Filamentous Phage (Ff) as Vectors for Recombinant DNA-A Review", *Gene*, V. 19, p. 1–10.

Hong, 1982, "A Systematic DNA Sequencing Strategy", *J. Mol. Bio.*, V. 158, 539–549.

Vieira et al, 1982, "The PUC Plasmids, an M13 mp7-Derived System for Insertion Mutagenesis and Sequencing with Synthetic Universal Primers", *Gene*, V. 19, 259–268.

Frischauf et al, 1980, "A Subcloning Strategy for DNA Sequence Analysis", Nucl. Acids Res., V. 8(23), 5541–5549.

Messing et al, 1982, "A New Pair of M13 Vectors for Selecting Either DNA Strand . . . ", *Gene*. V. 19, 269–276.

Barnes et al, 1983, "Kilo-Sequencing: Creation of an Ordered Nest of Asymmetric Deletions . . . ", *Methods in Enz*, V. 101, pp. 98–122.

Messing 1983, "New M13 Vectors for Cloning", *Methods in Enz*, V. 101, pp. 20–78.

Poncz et al, 1982, "Nonrandom DNA Sequence Analysis in Bacteriophage M13 by the Dideoxychain . . . ", *PNAS*, V. 79, pp. 4298–4302.

Maniatis et al, 1982, *Molecular Cloning a Laboratory Manual*, Cold Spring Harbor Lab., pp. 135–143.

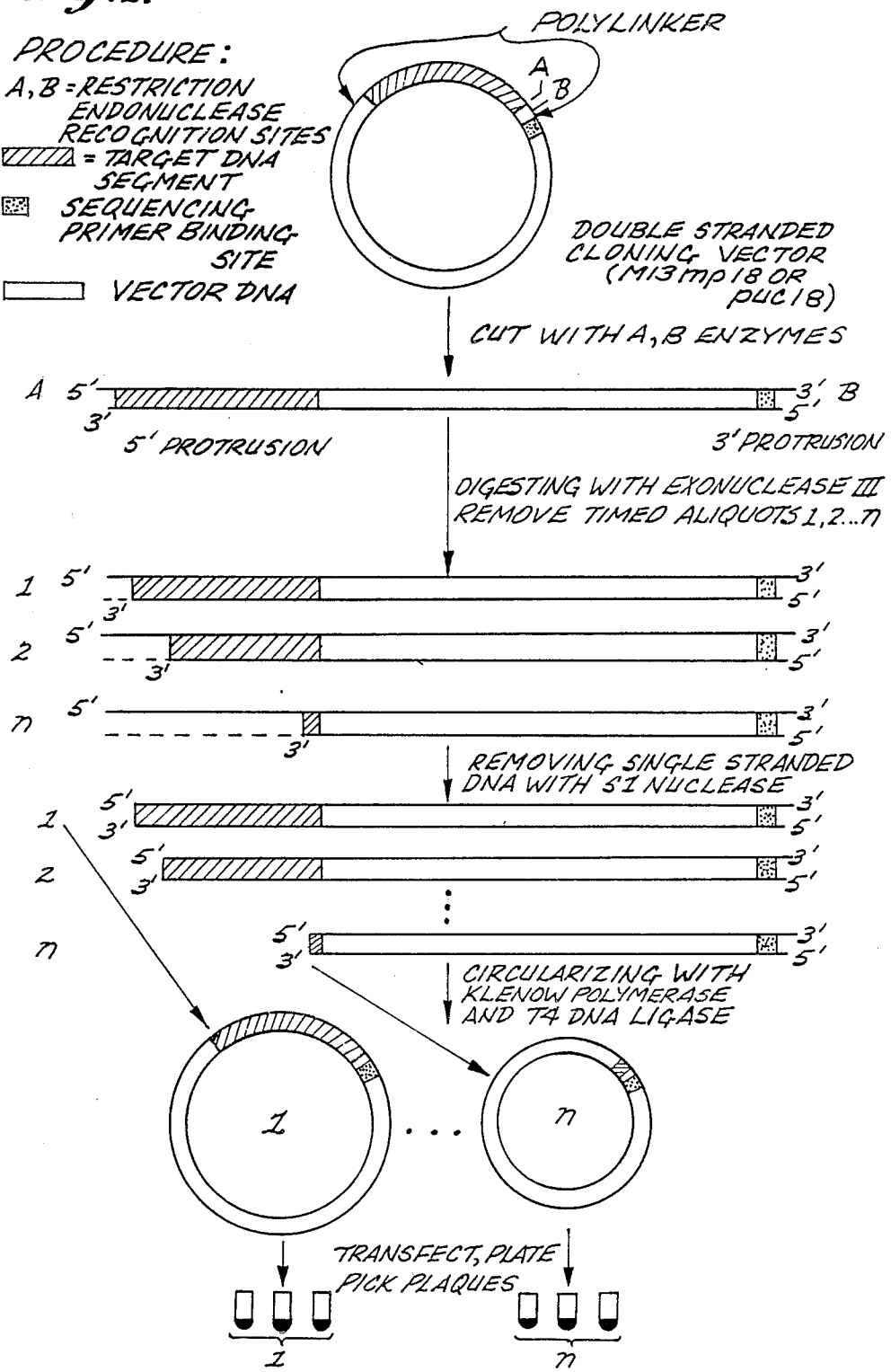

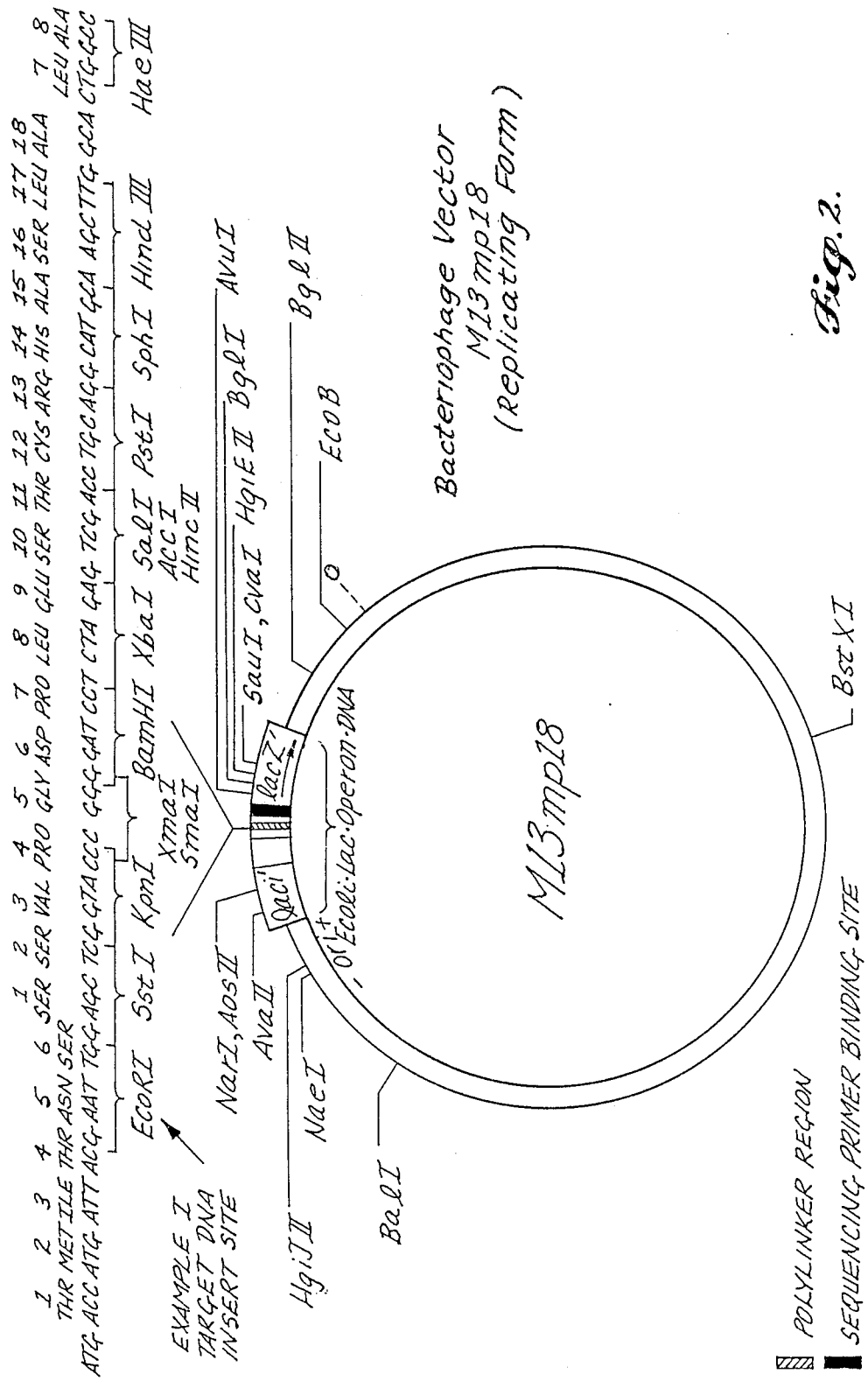

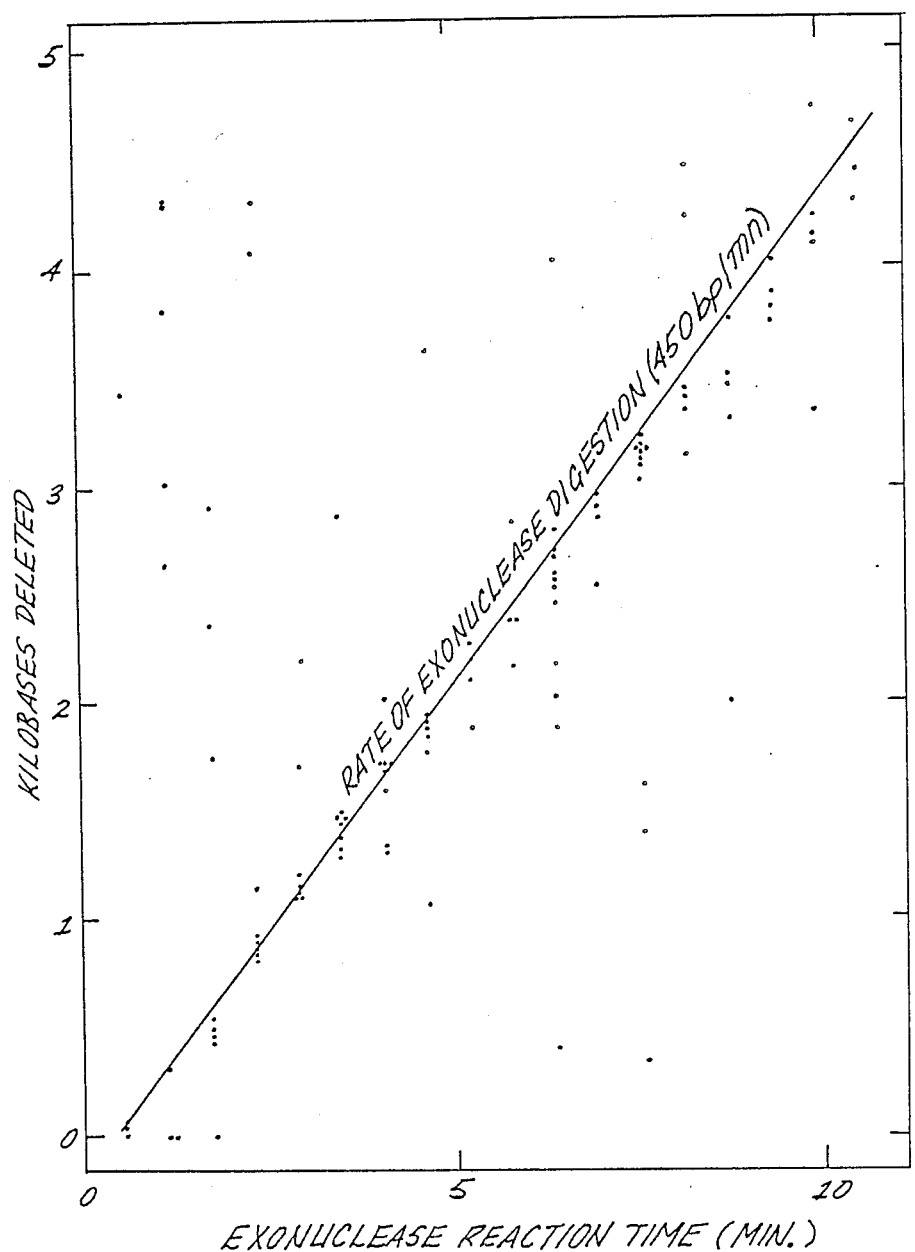
Fig. 3.   Distribution of Deletions

Fig. 4A.

```
        5' GAATTCGAAACCGACCCGGCCTTTAAACTTCGAATTCGGGCTGCTTT
-8100 TCGATCAACACGTGGGTGCCCATTAGTTCGTGTTATTGTTCCTCTGGGGAAACGTGATTAAGTCGAATTAGTCGATTAGTGGTTCCTCCACTCCAGCG
-8000 GAATTATGTCCCATCGGGTTCTGGTCATTGGCAGGCGGCCGGTCTGCTCGGAGCCACCGGATCTGCTCGGAAGTTGTCGCAATCTCCGAAGTGGCCCAAATATACGCA
-7900 CTGCCGGGTAGCCATGCCATCCAGCTGGTGGAGAAGTGCCGGATCTGGATGCCAAGACCTTGGATCTCAAGGATTTCGAGGTAGGTTCGTTACCCGAC
-7800 CTTGGAGCGACCTTCGTCGCGGTTCCTAAAGTTACTAAGAAAATGTCAAATGCCTTTATGGCTTCGTCGTGGTAAGAAACGCACTCCATGCTCGACGAGCACCTTTATGC
-7700 TTGGTTGCCATTTAATGCTGTTACCCAGTGATATTATTCGCTTTATGGCTTCATTGCATCCAATCTTGGTGCTCGGACGCCTTAACCCTTAGACGGGCCATGG
-7600 TGAGCGGCAGTCATAAATCCGTAATGCGACGCTGGGAAAACGTTTCATTGCATTGCGTTATTGGAAATATATTTTAAAAGTTTGCCACTATGCATCCACTGCTTAATT
-7500 GGGCGCAGTTGCACGTCTGGCTGATAAGTGATGTGTGATCTATCTCGTTATTGGAAATATATTTTAAAAGTTTGCCACTATGCATCCACTGCTTAATT
-7400 TTGTAAAGTATTTAATTTGTTGTATATATAAATCTACATATTAGTAAATTAAATTACAACATATAAATACATTTGTCATTGAGTACTCATTAACAACGTT
-7300 TTTCAAACTTAAATAAATGGTATACACAAAAACTACAACTGAAAGTGAACCAAAAACCAGTTTAATACATTATCTGCTTTAATTCGGTTAATTCGTTAATTAATAG
-7200 CAGGTAGCAGTGCCAAAAATTTAGATTCGATTTAGATTCAAAAATTACCTTTAAATTGGGCCTTTCCACTTTTATTCCTTTAATATATCTTT
-7100 CAAATGCGACTTTTCAACGATCCCATCATTATAGACTTTAAAGCGGACAACAGGTGTTATTTGGTTCGTTATTAAATAGGAAATTTGAATTCCAAAA
-7000 TATATTGGTTCAACAGTTAATAGGATTCCCCTAATTCTTAAACTCAATATCAATTATTAACTTCAGTCTCAATTGCTCGCATTTCAATGGATGCTTG
-6900 GGACAGACTTCTTTCAAATTGATTGCTCTGCCATAAACAGAATCGAATACCCAAAATGTTTATGTCGCTCCATGATGATCCATGATCCCCAGCAGAC
-6800 AACTCGACAGATCGATTACACTTTAGCTTATGTTGCTTAGCACTTCTATTTATTGTTCGTGGCTTAATTAATTGTTAGATCAAAATTCACAGATTCGC
-6700 CCGCTGGGCCCGCCAAGAGACCAGCCCCTTGCCCCGCCATAGAGTCACGTCCATCGATCATCAGTGCGTCGGAAGAGCTCGTCTCTGGGCCAGAGGTCGCG
-6600 ACGTGGTTCGTGGGCCGATCGTGCTCCACGGTCTTGAAGGTATATGTCTTGGGCGTGGCGGTGCCTCGGATTGGGGATCGTATGATCTGAATGTTGCGTGTGTACACATT
-6500 GAAGGCGGCTGCATCGTGCTCCACGGTCTTGAAGGTATATGTCTTGGGCGCTCCCCGGTGTAGTAGTCGTTGATCTGTGTAGGGATGCGTCCTAGTGTACTCCAGGGAGCCAGTATG
-6400 TAGTCCGGCCACCTGGGTCGTACGCGCCACGCCAAACTCATGCGCCGATGATAGCCAAACTCATGCGCCACATAGTTCACACTAATTACTTCGCCCTCGGGTGATGTGTAAC
-6300 TACTGCCCGCCCTGTACGGCCACGCCAATCCCTCCTGCGATGCGGAAATGCCATTGGAGGTCTCGTAGGCATACCGATACTTGCCATCCCGGCTCCAC
-6200 CTGCAGATCGTTCTGCAGGTGCGTGTTGCCAGGTCGCGGAAGTGCGAATCCCGGAAATTCCCGGAAATTTCGGGAAATTCCCATTTTCGGGAAATTCCCAGCTGATGCTTACAAGCAAATACATGGTGCGGTTCGAG
-6100 ACCTGTGGGCGGGATTCGAGACGAGAGTCGGCGATTATAATCCATTTTCGGGAAATTCCCAGCTGATGCTTACAAGCAAATACATGGTGCGGTTCGAG
-6000 TTTGGTTCTAAACTGCTTGCCTTCTCGGACGCTTCGTTTTATATCCATCCGCTCACCAGCAGCCTCACCAGGCCGATTTTGGCTATACATCGGCCTCGGAACCCAGT
```

Fig. 4B

PROCESS FOR PRODUCING SHORTENED TARGET DNA FRAGMENTS USABLE IN SEQUENCING LARGE DNA SEGMENTS

This invention was made with government support under Contract Nos. GM29009 and AM31232 awarded by the National Institutes of Health (NIH). The government has certain rights in this invention.

BACKGROUND OF THE INVENTION

The determination of the nucleotide sequence of DNA has become a routine analytical procedure for research in molecular biology. Current methods of sequencing involve the subdivision of a parent DNA segment into numerous, overlapping pieces all of which have one end in common. The pieces of different sizes are separated into different bands by a polya crylamide electrophoretic gel. The bands correspond to the nucleotides making up to the DNA sequence of each piece. The bands of all of the pieces are read off of the gel to obtain the complete sequence of up to about 300 nucleotides of DNA adjacent to the common end. The actual accumulation of sequence data for short (less than 300 nucleotides) DNA segments using this approach is relatively rapid if either the dideoxynucleotide triphosphate ("dideoxy") chain termination method of Sanger [Sanger, Nicklen and Coulson, Proc. Natl. Acad. Sci. (hereinafter, PNAS) USA, 74 (12), 5463 (1977)], or the chemical degradation reactions of Maxam and Gilbert [Maxam and Gilbert, Methods in Enzymology, 65,499 (1980)] are used.

While the complete sequence analysis of short DNA segments can be done relatively rapidly, the rapid, complete sequence analysis of long DNA segments (greater than 300 nucleotides) has proven significantly more difficult. This is due to the fact that electrophoretic gel band resolution exponentially decreases as the length of the piece of DNA to be electrophoresed increases. While separation between adjacent bands is readily visible when the pieces of DNA are less than approximately 200 nucleotides long, the exponential decrease in resolution of adjacent bands puts a practical upper limit of approximately 300 nucleotides on the length of a DNA segment that can be sequenced using a gel.

In the past, complete sequencing of long DNA segments by the Sanger method has been accomplished using a variety of techniques that involve the subdivision of the segment into smaller pieces followed by subcloning of the small pieces. These techniques make use of recombinant DNA technology, using DNA cloning vehicles and other tools of genetic engineering, to produce a cloned set of DNA pieces for sequencing. See Old and Primrose (Eds), *Principles of Gene Manipulation, An Introduction to Genetic Engineering*, 2nd Ed., University of California Press, (1981) for a survey of such techniques. The prior techniques may be classified into two broad groupings: (1) random subdivision of the parent DNA segment followed by random selection of subclones for sequencing [see Anderson, Nucl. Acids Res., 8, 5541 (1980); Messing, Crea and Seeburg, Nucl. Acids Res. 9, 309 (1981); Messing, Methods in Enzymology, 101, 20 (1983); and Sanger, Coulson, Hong, Hill and Peterson, J. Mol. Biol., 162, 729 (1982)]; and, (2) random subdivision of the parent DNA followed by nonrandom selection of subclones for sequencing [see Frischauf, Garoff, and Lehrach, Nucl. Acids Res., 8, 5541 (1980); Barnes, Bevan and Son, Methods in Enzymology, 101, 98 (1983), Barnes and Bevan, Nucl. Acids Res. 11, 349 (1983); Hong, J. Mol. Biol., 158, 4298 (1982); and Poncz, Solowiejzyk, Ballantine, Schwartz and Surrey, PNAS USA, 79, 4298 (1982)].

In the random subdivision/random selection approach to sequencing, long segments of DNA are randomly divided into smaller pieces. The pieces are subcloned into single-stranded phage vectors and selected at random. The major disadvantage with this technique is that complete sequencing of large segments becomes increasingly more tedious and, thus, more difficult when only a small portion of the sequence remains to be determined. This difficulty arises because the remaining small portions of DNA require the use of relatively time-consuming nonrandom sequencing procedures such as restriction enzyme analysis and further subcloning. Additionally, repeating portions of the sequence can cause ambiguities in the computer-assisted alignment of overlapping pieces.

The problems associated with random DNA sequencing techniques have led to the development of a second approach to the sequencing of long DNA segments. In this approach, the DNA segment to be sequenced, which is usually present as part of a circular recombinant DNA molecule is first broken at random to create linear DNA molecules. The linear DNA molecules are then cleaved with a restriction enzyme which is chosen so as to release the target DNA from the vector and which introduces a common end to be used for sequencing. The randomly divided target segments may be selected on the basis of size either before or after the final step of reinsertion into a cloning vector. This approach may also involve the introduction of a common site at different points located about 200–300 nucleotides apart in the long target DNA segment, which helps make all regions accessible to DNA sequencing methods after the steps mentioned above of release from the vector and size selection.

Hong (supra, 1982) describes the use of one form of this nonrandom selection technique to linearize cloned DNA by making double-stranded cuts in the M13 DNA molecule at random. He then cut, with a restriction endonuclease, the linear double-stranded DNA adjacent to the primer binding site on the M13 vector portion of the DNA molecule before recircularizing by ligation. This was followed by transfection of cells to produce a mixture of deletions wherein the primer binding site was placed adjacent to random points within the long DNA segment. Next, the nonrandom selection of deletion clones was attempted by the choice of bacteriophage plaques, since large plaques are made by bacteriophages with extensive deletions and small plaques are made by bacteriophages with small deletions. Unfortunately, this selection method was found to be extremely crude and unreliable.

Hong's technique is similar to an earlier approach which constructed deletions in DNA carried in plasmid vectors [Frischauf et al., supra, (1980)]. In that approach, the nonrandom selection was done using gel electrophoresis prior to circularization. Unfortunately, obtaining an ordered set of deletions that differ by only about 200 nucleotides for DNA carried in bacteriophage vectors has proven to be impractical because of the larger size of these vectors. Bacteriophage vectors are most useful for sequencing long segments of DNA because they allow the direct application of the Sanger dideoxynucleotide sequencing method.

Another nonrandom selection method is that of Poncz et al. (supra, 1982) wherein the exonuclease Bal 31 is used to obtain a set of randomly deleted fragments, which are subcloned into an M13 bacteriophage vector. As best understood, it appears as though this method suffers from the same difficulties as that of Hong (supra, 1982). The practicality of this method is also unclear since neither the cloning efficiency nor the actual distribution of deletion breakpoints in the segments are described in the Poncz publication.

Still another example is the nonrandom method of Barnes, Bevans and Son (Methods in Enzymology, supra, 1983), wherein infectious M13 bacteriophages were fractionated by agarose gel electrophoresis after random deletions were made in the inserted, target DNA by a series of enzymatic treatments. The result is a group of cloned DNA fragments with a succession of deleted intervals. For each interval, half of the deletion breakpoints are within 1000 nucleotides (Barnes and Bevan, supra, 1983). Although very long DNA segments can be usefully subdivided using this technique, random selection within each fairly large interval is necessary in order to obtain deletions that differ in length by approximately 200 nucleotides, necessary for sequence determination.

The advantages of nonrandom sequencing extend beyond sequencing of large DNA molecules. For example, nonrandom sequencing allows a particular region within a larger cloned DNA fragment to be targeted for dideoxy sequencing or other manipulations without the need of extensive prior knowledge of the restriction enzyme sites within that region. The deletions also can assist in mapping genes, regulatory regions, and even functionally significant regions within genes.

The strategies described briefly above represent prior attempts to subdivide a large segment into smaller overlapping intervals and to nonrandomly select the resulting subclones for sequence analysis. The main disadvantage of these techniques is that the size of the intervals between the generated deletions is generally larger (more than approximately 200 nucleotides) than can be practically sequenced without choosing and sorting a great many clones at random from each interval. Further, none of the above-described nonrandom methods offer significant advantages over purely random methods for sequencing a large DNA segment as attested to by the fact that none of the methods is widely employed at present.

In general, this invention describes a nonrandom process for initially generating overlapping shortened derivatives of a long DNA segment, suitable for DNA sequencing. As will be better understood from the following description, it differs from the methods described above which rely on random generation of deletions, primarily in that nonrandom selection is unnecessary. As a result of this difference, intervals between successive deletion breakpoints can be chosen which are sufficiently small to allow complete sequencing of long DNA segments.

SUMMARY OF THE INVENTION

In accordance with this invention, the nonrandom subdivision of a long target DNA segment is based on the unidirectional, synchronous enzymatic digestion of cloned DNA molecules that include the target DNA segment, in a manner that produces an ordered series of linear double-stranded DNA molecules. The length of the molecules is determined by the time of enzyme digestion. Times are chosen such that the linear DNA molecules differ from one another by small amounts of DNA (about 200 nucleotides). This nonrandom generation facilitates the rapid sequencing of long DNA segments without the need for less precise and time-consuming gel fractionation or other methods required by the methods described above. Additionally, this invention allows the rapid targeting of regions of interest in long DNA segments using the linear DNA molecule breakpoints obtained from the practice of the invention.

More specifically, in accordance with the present invention, there is provided a process for the rapid production of cloned, circular DNA molecules containing shortened target DNA segments derived from a long target DNA segment. Initially, a plurality of double-stranded circular recombinant DNA molecules are produced by molecular cloning. Each of the molecules includes: (i) vector DNA; (ii) a sequencing primer binding site; and, (iii) a DNA region having unique endonuclease sites and including the long target DNA segment. The plurality of double-stranded circular recombinant DNA molecules are cut by restriction endonucleases to create a plurality of double-stranded linear DNA molecules each having the long target DNA segment located at one end and the sequencing primer binding site located at the other end. The DNA molecules are unidirectionally sequentially shortened from the target end. At timed intervals, some of the shortened linear DNA molecules are removed. The shortened linear DNA molecules are reformed into circular DNA molecules. When this procedure is correctly followed, the reformed circular DNA molecules contain the original vector DNA and the shortened target DNA. The reformed circular DNA molecules are replicated and used in sequencing reactions to determine the complete nucleotide sequence of each strand of the original long target DNA segment. The long target DNA segment may contain 14,000 or more nucleotides (14 kb), and the cloning vehicle may be a plasmid or a bacteriophage.

In accordance with further aspects of this invention, the plurality of linear, double-stranded DNA molecules are shortened by exonuclease digestion. Further, the sequencing primer binding site end of the double-stranded linear DNA molecules are protected from, i.e., made immune to, exonuclease digestion, prior to exonuclease digestion. Thus, exonuclease digestion only takes place at the long target DNA segment end of the double-stranded linear DNA molecules.

In accordance with other aspects of this invention, the digestion exonuclease progressively digests (or removes) nucleotides at a uniform rate. Preferably, the exonuclease is exonuclease III.

In accordance with other aspects of this invention, the plurality of double-stranded recombinant filamentous bacteriophage DNA molecules each containing: (i) vector DNA; (ii) a sequencing primer binding site; and, (iii) a DNA region having unique restriction endonuclease sites and a long target DNA segment are produced by inserting a double-stranded long target DNA segment into double-stranded filamentous bacteriophage vectors, which include a sequencing primer binding site and a DNA region having unique restriction endonuclease sites. The double-stranded long target DNA segment is inserted into the DNA region having unique restriction endonuclease sites such that at least a portion of the DNA region having unique restriction endonuclease sites lies between the long target DNA segment and the sequencing primer binding site. Thereafter, the double-stranded filamentous bacteriophage DNA molecules resulting from said insertion are used to created said plurality of double-stranded recombinant filamentous bacteriophage DNA molecules each containing: (i) vector DNA; (ii) a sequencing primer binding site; and (iii) a DNA region having unique restriction endonuclease sites and a long target DNA segment.

In accordance with further aspects of this invention, the double-stranded filamentous bacteriophage vector into which said long target DNA segment is inserted is a derivative of the M13 filamentous bacteriophage DNA molecules isolated from an E. coli bacterial cell, preferably M13 mp18 or M13 mp19.

In accordance with yet other aspects of this invention, two restriction endonucleases are used to cut the plurality of double-stranded circular recombinant DNA molecules to create the double-stranded linear DNA molecules having the long target DNA segment located on one end and the sequencing primer binding site located on the other end. Preferably, one restriction endonuclease leaves a four nucleotide 3' protrusion at the sequencing primer binding site end and the other restriction endonuclease leaves a four nucleotide 5' protrusion at the target DNA segment end of the double-stranded linear DNA molecules. Alternatively, if other restriction endonucleases are used to cut the double-stranded circular recombinant DNA molecules, the ends of the resulting double-stranded linear DNA molecules may be treated enzymatically to achieve an end configuration such that the sequencing primer binding site end is not susceptible to exonuclease digestion and the target DNA segment end is susceptible to exonuclease digestion.

In accordance with yet still further aspects of the present invention, after the shortened linear DNA molecules are removed at the end of the timed intervals, they are treated with S1 nuclease, DNA polymerase I (Klenow fragment) and T4 DNA ligase. The S1 nuclease removes the single strand nucleotides from the target DNA segment end that remain after exonuclease digestion and the polymerase removes protruding nucleotides at the sequencing primer binding site end leaving blunt termini at both ends. The ligase reunites the blunt ends to create the reformed circular DNA molecules, which are replicated by transfection or transformation of bacterial cells to provide a plurality of cloned, circular DNA molecules each containing shortened target DNA segments. Taken together, the cloned circular DNA molecules can be used to determine the nucleotide sequence of the entire original long target DNA segment using conventional techniques. For example, a standard sequencing technique, such as the Sanger dideoxynucleotide triphosphate chain termination technique, can be used to sequence the collection of cloned, circular DNA molecules to determine the sequence of the long target DNA segment.

The entire procedure can be performed on a set of cloned circular DNA molecules containing one orientation of the long target DNA segment, then repeated on a set of cloned circular DNA molecules containing the other orientation, whereby both strands of the original, double-stranded DNA segment are completely sequenced. The results of the sequencing of one strand can then be compared with the other strand for accuracy.

The present invention can be used to assist in determining the nucleotide sequence of selected segments of target DNA in an efficient and economical manner. Because the invention makes use of recombinant DNA technology and enzymatic treatments to allow digestion of the target DNA segment without affecting the vector portion of the molecule, the prior art step of inserting derivative pieces into a new vector is avoided. Additionally, the present invention does not require tedious gel electrophoresis to subdivide fragments and isolate by size differentiation those useful in the sequencing reactions.

A further advantage of this invention is that the process can be used to pinpoint a preselected region in any molecule of the target DNA segment for further characterization or manipulation of genetic material.

BRIEF DESCRIPTION OF THE DRAWINGS

The advantages and features of the invention will be better understood by reference to the following description of a preferred embodiment of the invention when considered in conjunction with the accompanying drawings wherein:

FIG. 1 is a schematic outline of a preferred embodiment of the process of the invention;

FIG. 2 is a partial restriction endonuclease cleavage map for M13 mp18;

FIG. 3 is a graph showing the distribution of deletion breakpoints (kilobases deleted) as a function of exonuclease III digestion time, depicting the results of application of the process of the invention to the sequencing of a 4.5 kb EcoRI DNA segment of *Drosophila melanogaster* Gart locus;

FIG. 4A and B is the complete nucleotide sequence chart of the 4.5 kb EcoRI DNA *Drosophila melanogaster* Gart locus;

DESCRIPTION OF THE PREFERRED EMBODIMENT

Figures 5, 6:
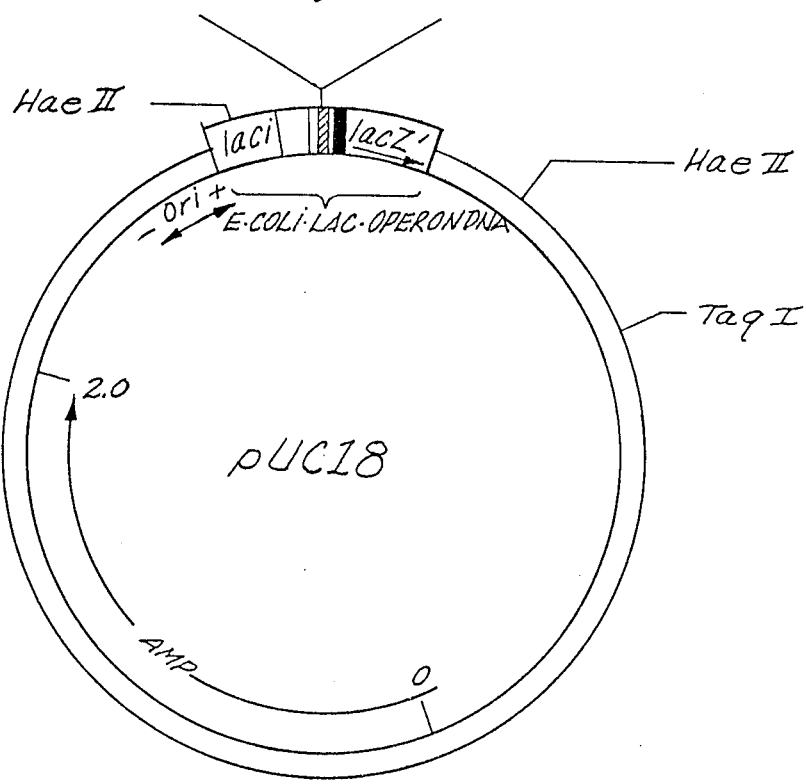
FIG. 5 is a diagram showing the one-way exonuclease III digestion of bacteriophage lambda DNA cleaved with SstI; and, FIG. 6 is a partial restriction endonuclease cleavage map for pUC18.

Due to the the fact that some terms used in the art to which this invention relates have different meanings to different people, it is believed that the process of this invention will be more easily understood if certain terms used in the description are first defined. Thus, as used herein the following terms have the noted meanings:

Cloning vehicle or vector—an extrachromosomal DNA molecule comprising a replicon (containing an origin of replication) which is replicated when placed within a suitable microorganism (the host), by a process called transformation or transfection. Examples are: plasmids that are double-stranded DNA molecules derived from resistance transfer factors; and bacteriophage vectors that are double-stranded or single-stranded DNA molecules in the case of the filamentous phages of E. coli isolated from virus-infected cells. Such vectors are able to carry inserted, exogenous DNA, target DNA, which will be duplicated in vivo, along with the vector DNA, in the process of replication.

Vector DNA—the part of a recombinant DNA molecule other than any inserted, exogenous DNA.

Target DNA segment—any DNA segment of interest which is excised from a selected genome and inserted into the polylinker region of the cloning vector. Shortened target DNA segments refer to the double-stranded part of an initial target DNA segment remaining after exonuclease digestion.

Recombinant DNA—composite molecules of DNA wherein exogenous DNA is carried by a vector DNA molecule, i.e., recombinant DNA denotes molecules comprising vector DNA and target DNA. The construction of these composite molecules is termed genetic engineering or molecular cloning.

Molecular cloning—the process by which a line of genetically identical molecules or organism are produced by propagating and amplifying the composite recombinant DNA molecule. Requires: techniques for cutting and joining pieces of DNA from different sources, transforming suitable host cells and identifying the resulting transformants.

Polylinker region—small DNA fragment containing several unique restriction endonuclease sites for cloning. In the M13 bacteriophage vector family it is inserted into the amino-terminal portion of the $\beta$-galactosidase gene, originally obtained from E. coli.

Basepair (bp)—a nucleotide and the complementary nucleotide opposite in the double-stranded DNA molecule. Also kilobase (pair) or (kb)—unit of bases (nucleotides) denoting either 1000 nucleotides or 1000 nucleotides and their complements.

Enzymatic digestion—the removal of nucleotides from the cleavage of a DNA molecule by enzymatic reaction.

Deletion—the removal of a contiguous stretch of nucleotides from a DNA molecule wherein an enzyme breaks the phosphodiester bonds connecting one nucleotide to another.

Deletion breakpoints—the points within the nucleotide sequence of a DNA molecule where breakage has occurred, for example, as a result of enzymatic action within the nucleotide sequence of a DNA molecule. Used to target sequences within a DNA molecule for sequencing or other molecular manipulations.

Restriction endonuclease—enzymes which cut (restrict) duplex DNA molecules into discrete pieces. The enzymes interact with a recognition sequence of nucleotides in the duplex DNA. Restriction endonucleases used in molecular cloning cut the DNA molecule within a particular sequence of nucleotides. There are several types of these enzymes, each with different properties and designated by specific nomenclature.

Exonuclease III—an enzyme from E. coli catalyzing the stepwise removal of 5' mononucleotides in the 3' to 5' beginning at the 5' protuding or blunt termini of double-stranded DNA. Used to delete nucleotides from the termini of DNA fragments, and is usually followed by S1 nuclease treatment.

Large fragment of DNA Polymerase I (Klenow fragment) (E. coli)-an enzyme consisting of a single polypeptide chain which has both 5' to 3' polymerase activity and exonuclease activity in the 3' to 5' direction. This enzyme leaves blunt ends by either polymerizing nucleotides complementary to a 5' protrusion or digesting nucleotides constituting a 3' protrusion.

Nuclease S1—an enzyme that digests single-stranded DNA.

T4 DNA Ligase—(from bacteriophage T4 infected E. coli) an enzyme catalyzing the formation of phosphodiester bonds between adjacent 3'-OH and 5'-P termini in DNA. Used to ligate cohesive or alternatively, blunt ends of DNA fragments together of blunt ends together.

Agarose gel electrophoresis—a widely used laboratory technique to separate DNA of different molecular weights. The migration of double-stranded DNA in the gel is inversely proportional to the logarithm of molecular weight. This migration is visualized by staining the bands of DNA in the gel with dye and examining the gels in ultraviolet light.

Polyacrylamide gel electrophoresis—a widely used laboratory technique used to separate macromolecules. When used to separate labeled denatured DNA fragments to be detected by autoradiography, this technique can form the basis of DNA sequencing by either the Sanger dideoxy or the Maxam-Gilbert chemical sequencing techniques. Migration of DNA is inversely proportional to the logarithm of molecular weight.

GENERAL DESCRIPTION

As illustrated in FIG. 1, the process of the present invention produces a plurality of cloned, circular DNA molecules each containing shortened target DNA segments, and all derived from a long target DNA segment using enzymatic and recombinant DNA techniques. The cloned, circular DNA molecules are suitable for use in determining the nucleotide sequence of the long target DNA segment. To this end, recombinant DNA molecules are constructed, each of which includes a vector DNA region, a sequencing primer binding site and a DNA region that contains unique restriction endonuclease sites and the long target (e.g., exogenous) DNA segment. The sequencing primer binding site is separated from the long target DNA segment by at least some portion of the DNA region having unique restriction endonuclease sites.

The foregoing cloning vehicle is replicated to produce a plurality of double-stranded circular recombinant DNA molecules each containing the long target DNA. The circular recombinant DNA molecules are cut by restriction endonucleases to produce a plurality of double-stranded linear DNA molecules, each having the long target DNA segment at one end and the sequencing primer binding site at the other end. More specifically, the recombinant circular DNA molecules are cut by two restriction endonucleases. One restriction endonuclease cuts the molecule in a manner that leaves a terminus that is susceptible (or may be made susceptible), to digestion by an exonuclease. The other restriction endonuclease leaves a terminus that is protected (or may be made protected) from digestion by an exonuclease. The terminus that is susceptible to exonuclease digestion is at the long target DNA segment end of the double-stranded DNA molecules and the terminus that is protected is at the sequencing primer binding site end.

The plurality of double-stranded linear DNA molecules containing the long target DNA at one end are then subjected to excess amounts of an exonuclease enzyme, which digests one strand of the double-stranded linear DNA molecules from the long target DNA end. At timed intervals, portions of the digested double-stranded linear DNA molecules are removed. The removed linear molecules are digested by a single-strand specific nuclease to remove the undigested strand. The result is a series of overlapping double-stranded, linear DNA molecules containing shortened, target DNA segments. The thusly created linear DNA molecules are circularized to reform double-stranded DNA molecules containing vector DNA and shortened target DNA segments. Thereafter, the reformed circular DNA molecules are replicated by molecular cloning, producing many copies of the overlapping, shortened target DNA segments for sequencing by well-known methods.

PREPARATION OF PARENT RECOMBINANT DNA MOLECULES

In accordance with the present invention, the DNA segment of interest (e.g., the long target DNA segment) is cloned and isolated in double-stranded form by any of a variety of excision techniques. The DNA segment is inserted into the polylinker region of a suitable cloning vehicle and selected and amplified by well-known techniques.

The procedures and materials for preparing and cloning recombinant vectors are discussed in Old and Primrose, (supra 1981), which is incorporated herein by reference to the extent necessary to an understanding of the present invention.

The process of this invention depends on in vitro manipulation outside of the host cells of recombinant DNA molecules containing the target DNA segment to be sequenced. Thus, the invention is not dependent on the host system selected. The cloning vehicle used in the present invention may be a DNA molecular cloning vector such as a bacteriophage or plasmid. Thus, animal, bacterial and yeast cells may be selected as host cells. For reasons described below, a bacteriophage vector which occurs in both single- and double-stranded forms, is preferred.

Suitable bacteriophage or plasmid DNA molecules can be obtained from commercial sources. The particular vector chosen should be compatible with the cells serving as the host. Further, the size of the chosen vector should be sufficient to stably accommodate the length of target DNA segments to be sequenced. At the present time, the preferred bacteriophage DNA molecules are from the M13 family, namely M13 mp18 and M13 mp19, which can be obtained from Bethesda Research Laboratories, Inc., P.O. Box 6009, Gaithersburg, MD 20877.

The filamentous bacteriophages of the M13 family, which were developed by J. Messing (supra 1983), have proven convenient for use as vectors for molecular cloning research and especially for DNA sequencing. These M13 bacteriophage vectors of Messing contain an intergenic region of approximately 500 basepairs, which accepts inserts of exogenous DNA without interfering appreciably with virus viability. One type of recombinant vector contains a small DNA segment (a polylinker) inserted in the double-stranded or replicative form (RF) of the M13 viral DNA. This polylinker consists of DNA containing a series of unique endonuclease restriction sites inserted into the amino-terminal portion of the $\beta$-galactosidase gene (derived from *E. coli*), which has been inserted by Messing into M13. The various M13 vectors developed by Messing thus differ primarily in number and order of the restriction enzyme sites found in the polylinker region. Foreign or "target" DNA segments may be inserted into the polylinker region. Phages that contain a target DNA segment inserted into the polylinker region of the vector DNA molecule can be detected growing in a lawn of *E. coli* cells plated in agar containing a chromophore and IPTG as colorless plaques, because the insertion of DNA into the polylinker activates the $\beta$-galatosidase gene [Old and Primrose, supra, (1981)]. Recently, Messing has made commercially available two new M13 cloning vectors, M13 mp18 and M13 mp19, each with ten unique endonuclease restriction sites, (the polylinker regions of M13 mp18 and M13 mp19 are mirror images of each other.) See FIG. 2, which is a partial restriction endonuclease cleavage map of M13 mp18.

As noted above, bacteriophage of the M13 family are filamentous phages each containing a single-stranded circular DNA molecule that can infect *E. coli* bacteria. When the single-stranded viral (phage) DNA passes into a host cell, it is converted into the double-stranded (replicative) form. Only one strand of this form (the plus strand) is amplified into single-stranded, circular DNA molecules. These molecules are packaged as phage particles and released by the infected cells into the medium. Single-stranded DNA molecules can be purified from the released phage particles and double-stranded circular DNA forms can be purified from infected *E. coli* cells. Additionally, phage DNA can be introduced into host cells by infection and double-stranded forms of the phage DNA can be introduced into host cells by transfection. Especially useful is the fact that the single-stranded form provides a convenient template for DNA sequencing using the Sanger dideoxy chain termination sequencing reactions. Additionally, the M13 vectors have been constructed with a polylinker region that facilitates the insertion of DNA in a manner that allows sequencing to be done by the Sanger dideoxy nucleotide procedure using a single sequencing primer binding site (See Messing, supra 1983).

Returning now to the invention, recombinant DNA molecules containing the DNA segment of interest are used to transfect suitable host cells by standard methods (Messing, supra 1983). Transfected cells are plated in a medium containing isopropylthiogalactoside (IPTG) and the chromophore X-gal. Cells that contain the recombinant bacteriophage with the inserted long target DNA segment inactivate the *E. coli* gene $\beta$-galactosidase carried on the vector and yield relatively clear areas on the plate that are easily distinguished from the blue areas where cells are transfected with bacteriophage that lack the inserted long target DNA segment. These areas, called plaques, arise from a single host cell transfected with a single molecule, releasing bacteriophage containing recombinant, single-stranded circular DNA molecules identical to the plus strand of the original transfecting molecule. A single plaque, which appears on the plate after many cycles of infection, may be collected and used to reinfect fresh cells to amplify the amount of recombinant DNA.

As noted above, the preferred bacteriophage vectors used to carry out the process of the invention are two M13 derivatives, namely M13 mp18 and M13 mp19, each of which contain ten (10) unique restriction sites in a polylinker region. When a long target DNA segment is inserted in the polylinker region of the vector such that at least two of these restriction sites lie between the target DNA segment and a sequencing primer binding site, cleavage at the restriction sites using two appropriate endonucleases results in a protrusion of nucleotides at the 5' terminus adjacent to the target DNA segment, and a protrusion of nucleotides at the 3' terminus adjacent to the sequencing primer binding site (see FIG. 1). In order to preserve the entire long target DNA segment intact in the resulting linearized DNA molecule, the two chosen restriction endonucleases must not cleave within the long target DNA segment. When M13 mp18 or M13 mp19 is used as the cloning vector, it has been determined that the likelihood of being able to find restriction endonucleases that do not cleave within the target DNA segment is approximately 80% for 4 kb DNA segments.

If a plasmid is selected as the cloning vehicle, the preference is for it to be constructed with an inserted polylinker region that can accept the inserted target DNA segment, which contains unique restriction sites such that restriction with the appropriate endonucleases produces linearized DNA molecules having the desired termini. The best current plasmid in this regard is one which includes the same polylinker found in an M13 mp18 or M13 mp19 bacteriophage vector as described above. Such a plasmid is pUC18 (and its mirror image pUC19). See Norrander et al., supra, (1984). This plasmid is capable of replication in *E. coli* and contains a phenotypic marker, a gene coding for ampicillin resistance, to enable the transformed host cells to be readily isolated from culture. A partial restriction endonuclease cleavage map of this plasmid is shown in FIG. 6.

Regardless of the nature of the cloning vehicle, the excised, double-stranded, target DNA segment isolated from the selected genome is inserted into the chosen cloning vehicle (plasmid or bacteriophage vector) by ligation, using well-known techniques. If the vector is a double-stranded bacteriophage vector, the target is inserted into the polylinker region and the recombinant DNA molecule is then used to transfect a suitable host organism such as the bacteria *E. coli* (strain 71-18 or JM107). If the vector is a plasmid the target DNA is also inserted into the polylinker and the plasmid is introduced into an appropriate host, such as *E. coli* (strain IIR or HB101), by transformation using established methods.

Transformants are then isolated and analyzed for the presence of the inserted target DNA segment. The isolated transformants may also be analyzed to determine if both orientations of the inserted target DNA segment are present. In this regard, if the vector used is a bacteriophage M13 vector, the recombinant DNA molecules that result from transfection are screened to identify those that contain the target DNA segment inserted in one orientation and those that contain the target DNA segment inserted in the opposite direction. Present sequencing methods require both orientations of the target DNA segment for accuracy since only one strand of the vector is replicated and present in the single-stranded DNA molecule contained in phage released from culture. This screening is accomplished using limited sequence ("T-track") analysis followed by electrophoresis and autoradiography which yields sequence data for up to 200 nucleotides in fragments of DNA.

T-track analysis [Anderson, Nucl. Acids Res., 9, 3015, (1981)] uses one of the four dideoxynucleotide triphosphate termination sequencing reactions (normally dideoxythymidine, triphosphate, ddTTP) to screen the fragments, by identifying those which vary in length by some predetermined amount. It can also be used to assist in identification of cloned recombinant DNA molecules carrying opposite orientations of inserted, target DNA segments. The only chain terminating nucleotide analog present is ddTTP, and when the reactions for the clones are subjected to electrophoresis, the gels indicate a pattern of T and non-T residues in the linear DNA molecules being sequenced. Thus, this procedure also allows deletions which cover the whole span of the target DNA to be identified and selected for complete sequencing by the dideoxynucleotide chain termination method (Sanger et al., supra, 1977).

Recombinant DNA molecules may be further characterized by complementation ("C"-test) analysis to confirm that vectors containing both orientations of the inserted target DNA segment are isolated (Example I). C-test analysis involves hybridization and agarose gel electrophoresis of two, separate single-stranded DNA samples which may have previously been studied by T-track analysis and contain different orientations of the inserted target DNA segment. If each of the samples represent one of two possible orientations, the rate of migration of a mixture of the samples is slower than the rate of migration when each sample is electrophoresed separately. The slower migration indicates the two samples are complementary, confirming that the DNA is inserted in opposite directions.

After the transformants are isolated and analyzed, recombinant bacteriophage M13 vectors containing both orientations of the target DNA segment are multiplied in and isolated from infected cultures of *E. coli*, as bacteriophage particles. The particles containing single-stranded DNA is then used to reinfect *E. coli* to create the replicative (double-stranded) form of the M13 vectors.

Where the recombinants are plasmids, the molecules are screened by restriction mapping to identify clones carrying both orientations of target DNA. In most instances, sufficient double-stranded DNA will be obtained from the screening whereby no further amplification and growth will be necessary before proceeding to the next step of the process of the invention.

LINEARIZATION OF PARENT DNA MOLECULES

The thusly cloned DNA molecules containing both orientations of the target DNA segment are cleaved with selected restriction endonucleases. These restriction endonuclease enzymes are chosen on the basis that they will cleave at restriction sites located in the polylinker region lying between the inserted target DNA segment and the sequencing primer binding site (see FIG. 1). One restriction endonuclease cleaves at a site located adjacent to the target DNA segment in a manner that produces a terminus that is susceptible, or can be modified to be susceptible, to digestion by an exonuclease, such as exonuclease III. The other restriction endonuclease cleaves at a site located adjacent to the sequencing primer binding site in a manner that produces a terminus that is immune to digestion by an exonuclease, or that is capable of being modified to become immune to such digestion. As a result, linear DNA molecules having the inserted target DNA segment located at one end and the sequencing primer binding site located at the other end are created. If desired, the cleaving enzymes may be simultaneously used to cut the parent DNA molecule. Two enzymes that can be simultaneously used to cleave M13 mp18 or pUC18 are Sal I, which leaves a four nucleotide, 5' protusion terminus adjacent to the target DNA segment, and Sph I, which leaves a four nucleotide, 3' protusion terminus adjacent to the sequencing primer binding site. The short piece of polylinker DNA located between the two enzyme restriction sites created by the enzymatic cleavage is removed during the subsequent exonuclease digestion and can be disregarded.

It is the configuration of the termini produced during the cleavage or cutting step using the two restriction endonucleases that makes the linear DNA molecules susceptible to unidirectional exonuclease digestion. The terminus of the target DNA segment end of the linear DNA molecule must be susceptible to exonuclease attack, and the sequencing primer binding site end must be immune to such attack in order for the invention to work. As described above, when Sal I and Sph I are the restriction enzymes, Sal I leaves a four nucleotide 5' terminus, and Sph I leaves a four nucleotide, protrusion at the 3' terminus. A four nucleotide, 5' terminus is susceptible to exonuclease digestion and the four nucleotide, 3' terminus is not. As will be understood by those skilled in exonuclease digestion, the number of nucleotides that protrude at the 5' end is not critical. An enzyme leaving 0–3 nucleotides protruding at the 5' end can be used to carry out this aspect of the invention. On the other hand, if fewer than four nucleotides protrude at the 3' end, addition of extra nucleotides using an enzyme terminal deoxynucleotide transferase and well-known methods may be necessary to make the end immune to exonuclease digestion. Additionally, it is pointed out that a 5' protrusion remaining after cleavage could be blocked from exonuclease digestion using large fragment (Klenow) DNA Polymerase I and alpha-phosphorothioate deoxynucleotide triphosphates [See Putney, PNAS USA 78;7350 (1981); Jasin, Regan and Schimmel, Nature 306; 441 (1983)]. Further, a four nucleotide 3' terminus, normally immune to exonuclease attack, can be made susceptible by treatment with large fragment (Klenow) DNA Polymerase I. Use of materials such as these and others allows a wide variety of restriction endonuclease enzymes to be used to cleave since a terminus of unacceptable form can be enzymatically modified to create a terminus of the desired form.

Another way to extend the range of restriction endonucleases that can be used to carry out this invention is to construct cloning vectors with a greater number of restriction endonuclease cleavage sites. In particular, two commercially available restriction enzymes, Not I and Sfi I (New England Biolabs, Inc., 32 Tozer Road, Beverly, MA 01915), cleave within 8 basepairs of one another. Neither enzyme's recognition site is likely to occur within any particular target DNA segment that can be cloned into a filamentous bacteriophage. While Sfi I might not adequately protect adjacent DNA sequences from exonuclease digestion at 37° C., the addition of extra nucleotides to 3' termini using the enzyme terminal deoyxnucleotide tranferase after cleavage will protect that terminus from digestion. Inserting Not I and Sfi I recognition sites within the polylinker, allows larger DNA segments to be inserted into the polylinker without prior restriction analysis.

UNIDIRECTIONAL DIGESTION OF LINEAR, DOUBLE-STRANDED DNA MOLECULES WITH AN EXONUCLEASE

The double-stranded linear DNA molecules, produced by cleavage of the double-stranded circular recombinant DNA molecules by the preferred endonucleases described above, have nucleotide 5' and 3' protrusion termini (FIG. 1). Certain exonucleases, such as exonucleases III (E.C. No. 3.1.11.2), are known to catalyze the sequential removal of nucleotides in the 3' to 5' direction from the 5' protruding termini of double-stranded DNA, while 3' protruding termini are not significantly digested. More specifically, exonuclease III digests double-stranded DNA molecules by removing nucleotides successively from each 3' terminus, leaving extensive single-stranded protrusions of nucleotides at the 5' terminus of the linear molecule. [Wu, Ruben, Siegel, Jay, Spielman and Tu, Biochemistry, 15, 734 (1976).] However, exonuclease III fails to digest termini with four base 3' nucleotide protrusions, although blunt ends and all 5' protrusions are susceptible to attack [Guo and Wu, Nucl. Acids Res., 10, 2065 (1982).] Exonuclease III moves synchronously (at a uniform rate) when in excess and at temperatures up to 37° C. [Wu, et al., supra (1976).] We have found that this synchrony is maintained for relatively long digestion times (see the following Examples). When followed by digestion with S1 nuclease (or any single-strand specific nuclease), exonuclease III can be used to progressively shorten DNA fragments for the construction of deletions [Maniatis et al., *Molecular Cloning, A Laboratory Manual*, Cold Spring Harbor Laboratories, New York, (1982); Jasin et al. supra, 1983.]

The foregoing properties of exonuclease III are capitalized on by this invention to achieve the unidirectional synchronous digestion of one end of the linear double-stranded DNA molecules produced by endonuclease restriction. The susceptible end contains the target DNA (FIG. 1). As will be better understood from the following discussion, digestion at a uniform rate is a significant beneficial feature of the present invention.

Digestion is accomplished by adding exonuclease III to a solution of the linear DNA molecules produced by restriction of the circular recombinant DNA molecules, to give a molar excess of enzyme over DNA. To obtain rapid uniform digestion at a constant rate, the reaction is conducted at 37° C. Aliquots (small samples of identical volumes) of the reaction mixture are removed and separately processed at timed intervals and the reactions stopped to produce a series of samples containing successively shortened linear DNA molecules. Each sample represents a corresponding time interval of exonuclease digestion. The samples are selected to cover digestion of the entire target DNA segment. Successive samples give rise to successive clusters of deletion breakpoints. Further, the DNA molecules in the samples overlap one another due to the fact that earlier removed samples contain all of the nucleotides of later removed samples, plus additional nucleotides. See FIG. 1.

It will be appreciated that any exonuclease that uniformly digests one or both strands of a double-stranded molecule, but which is not able to digest 3' protruding termini or termini that can be blocked from digestion of a selected terminus, may be used in this invention. Similarly, any exonuclease, such as lambda exonuclease, that uniformly digests one or both strands of a double-stranded molecule but which is not able to digest 5' protruding termini or termini that can be blocked from digestion of a selected terminus, may also be used in this invention.

The actual rate of exonuclease digestion under the particular conditions selected for carrying out this invention, can be determined by examining portions of the aliquots which are withdrawn at timed intervals from the exonuclease digestion reactions as above. Examination involves electrophoresis of the removed portions on an agarose gel. The molecular weight of the digested DNA, which corresponds to a specific time of digestion, is determined by comparison to molecular weight standards also electrophoresed on an agarose gel. This procedure also enables selection of the aliquots to be used for sequencing any selected region of the target DNA, based on the extent of exonuclease digestion.

Each double-stranded linear DNA molecule produced in the manner described above has one strand of the target DNA segment deleted corresponding to the time of its exposure to exonuclease. In order to remove the strand complementary to the strand deleted by the exonuclease, the shortened linear DNA molecules are treated with a single-strand specific nuclease. A preferred nuclease is the S1 Nuclease from *Aspergillus oryzea*, although others with similar single-stranded specificity, such as mung-bean nuclease, may be used. The result of single-stranded nuclease digestion is a collection of double-stranded linear DNA molecules each containing target DNA that has been shortened by an amount that corresponds to the time of exonuclease digestion.

RECIRCULARIZATION OF DNA MOLECULES CONTAINING DELETED TARGET DNA FOR TRANSFORMATION

The shortened linear DNA molecules created by deleting part of the target DNA segment by exonuclease digestion are next circularized for transformation of a suitable host. Circularization is accomplished by successive treatments with large fragment (Klenow) DNA polymerase I and $T_4$ DNA ligase. The polymerase blunts the 3' nucleotide protrusion or 5' nucleotide protusion ends, which usually exist after S1 nuclease treatment of double-stranded DNA molecules. The polymerase removes 3' protrusions because of a 3' to 5' exonuclease activity that does not require deoxynucleotide triphosphates. The polymerase also converts 5' protrusions into blunt ends in the presence of deoxynucleotide triphosphates. Therefore, addition of this enzyme to a solution containing linear DNA molecules with either or both 3' and 5' protrusions, followed by addition of the four deoxynucleotide triphosphates, results in the conversion of all ends to blunt ends, which then serve as substrates for a suitable DNA ligase, such as $T_4$ DNA ligase.

$T_4$ DNA ligase catalyzes the formation of phosphodiester bonds between two blunt ends of double-stranded linear DNA molecules. In relatively dilute solutions of linear DNA molecules, such as those produced by the treatments described above, circularization of the linear molecules is favored over end-to-end joining of separate molecules (See Old and Primrose, supra, 1981). Accordingly, in accordance with this invention, the shortened linear DNA molecules that have been "blunt-ended" with DNA polymerase I are diluted into a solution suitable for ligation that contains a ligase, preferably $T_4$ DNA ligase. Such treatment leads to efficient circularization of the deleted linear DNA molecules and makes them suitable for transfection or transformation. This circularization procedure eliminates the need for excising the shortened target DNA segments from the linear DNA molecules and, then, inserting the excised target DNA segments into separately prepared cloning vectors.

The reformed circular DNA molecules collectively comprise an overlapping, ordered series that represents the entire target DNA. After being formed, they are amplified for sequencing by cloning a number of molecules. This molecular cloning is accomplished by well-known techniques involving the transformation or transfection of an appropriate host cell and the isolation of the resulting cloned DNA molecules. In the case where the cloning vector DNA is derived from a bacteriophage, such as M13, preferably, the recircularized DNA molecules are used to transfect competent *E. coli* cells. Infected cells (indicating the presence of the bacteriophage) are detected by plaques which form amidst a lawn of growing cells plated on agar. Thus, cloned DNA molecules containing the deleted target DNA are easily identified and removed for the sequencing reactions. Alternatively, if a plasmid such as pUC18 is used as the vector DNA, cloning of recircularized DNA molecules are preferably carried out by the transformation of appropriate host cells such as *E. coli* strain and the isolation of plasmid DNA from host colonies using well-known techniques.

As will be readily appreciated from the foregoing description, the invention produces an ordered set of cloned DNA molecules with successively shortened target DNA segments that, when taken together, cover the entire sequence of the long target DNA segment. The utility of cloned DNA molecules containing successively shortened target DNA for DNA sequencing lies in the practical limitations of DNA sequencing techniques based on the resolution of polyacrylamide gel electrophoresis. Such techniques only allow about 200 nucleotides of a DNA segment to be determined in the vicinity of a sequencing primer binding site (for the Sanger dideoxynucleoxide technique) or in the vicinity of a restriction endonuclease cleavage site (for the Maxam-Gilbert chemical degradation technique). By choosing cloned successive DNA segments with intervals between segments of 200 nucleotides or less, the invention can be used to determine the sequences of long DNA segments. The intervals comprise an amount of additional target DNA in a reformed circular DNA molecule when compared to the reformed circular DNA molecule with the next shortest target DNA segment. Thus, when taken together, the sequences of successive intervals comprise the entire target DNA segment.

In the case where the shortened target DNA segments are inserted in M13 vectors, bacteriophage DNA containing the target DNA segments are isolated from the transfected *E. coli* cells in single-stranded form. These isolated molecules are then used directly as the template for sequencing using the dideoxynucleotide triphosphate chain terminating reactions of (Sanger et al., supra 1977). Alternatively, the chemical degradation method of Maxam and Gilbert may be used to sequence the deleted DNA molecules produced by the invention. In the latter case, the double-stranded replicative form of the clone to be sequenced is isolated using well-known standard methods (Messing, supra 1983) and sequence determination is carried out after first incubating with a restriction endonuclease that cleaves adjacent to the deletion breakpoint. The Sanger sequencing reaction method is preferred because it avoids the more laborious steps of the Maxam-Gilbert technique.

In the case where plasmids are the cloning vehicles used in this invention, since they are normally not produced in single-stranded form within their respective host cells, the double-stranded recombinant DNA molecule must be treated to produce partially single-stranded, circular DNA molecules prior to dideoxynucleotide triphosphate sequencing. This may be accomplished by denaturing and rapid renaturing of the circular, double-stranded plasmid DNA molecules, leaving imperfectly reannealed circles with single-stranded regions that can be primed for DNA sequencing by the Sanger dideoxynucleoxide method. As with bacteriophage vectors, the Maxam-Gilbert method of sequencing may be used with plasmid vectors even though, again, it is more tedious.

EXAMPLE I

Application of the Process to a 4.5 kb Ecori DNA Segment from the *Drosophila Melanogaster* Genome This example describes an experiment wherein the sequence of a long target DNA segment taken from a region within a particular genome that has been previously characterized is accurately determined using the process of the invention.

Step 1. Purification and Cloning of a 4.5 Kilobase EcoRI DNA Segment

Lambda Charon4 clones of *Drosophila melanogaster* genomic DNA have been found to include DNA sequences derived from the GAR transformylase (Gart) locus [Henikoff, Sloan and Kelly, Cell 34,405 (1983). A 4.5 kilobase double-stranded EcoRI DNA segment was isolated from a lambda Charon-4 clone by digesting with the restriction endonuclease EcoRI using established techniques. This digestion provided a segment with cohesive ends for insertion into the EcoRI recognition site within the polylinker region of a M13 mp18 double-stranded (replicative form) bacteriophage vector. This vector was previously isolated from infected *E. coli* using standard techniques (Messing, supra, 1983). Ligation was accomplished in the usual manner using T4 DNA ligase.

Vectors containing the inserted EcoRI DNA segment were used to transfect *E. coli* 71-18 cells by standard methods (Messing, supra 1983). Transfected cells were plated in soft agar containing isopropylthiogalactoside (IPTG), the chromophore X-gal and exponentially growing 71-18 cells. Plates were incubated overnight at 37° C. (Messing, supra, 1983). This gave a distribution of blue and colorless plaques; plaques with the inserted target DNA segment at the EcoRI site are colorless. These plaques were collected by using toothpicks and the recombinant bacteriophage used to infect 2 ml test tube cultures of fresh *E. coli* cells.

Step 2. Selection of Recombinant DNA Molecules Containing 4.5 Kilobase EcoRI DNA Segments Inserted in Opposite Orientations The 4.5 kb EcoRI DNA segment was inserted in opposite orientations in the M13 vector obtained in Step 1. Both orientations of cloned inserted target DNA segments are necessary for accurate DNA sequencing of the insert. Both types of clones were identified using limited sequence or "T-track" analysis.

Supernatants containing bacteriophages from the test tube cultures of infected *E. coli* cells produced in Step 1 were used to prepare single-stranded DNA for T-track analysis. Each sample of purified DNA was annealed in the usual manner to an oligonucleotide primer that binds adjacent to the polylinker region of the M13 mp18 vector. A mixture of labeled and unlabeled deoxyribonucleotides (dNTPs) and one of the four dideoxyribonucleotide triphosphates (dideoxythymidine, ddTTP) was added to the samples for sequence determination by the widely known Sanger dideoxynucleotide triphosphate chain termination method, except that only one (ddTTP) of the four reactions was performed for each template.

After electrophoresis and autoradiography, the DNA cloned in the M13 mp18 vector showed up in two patterns, which presumably corresponded to the same EcoRI-generated long target DNA segment inserted in opposite orientations. An example of each orientation pattern was selected for complementation test analysis to confirm opposite orientations (Messing, supra 1983). Two different single-stranded DNA samples were mixed together in approximately 0.2M NaCl at 67° C. and then applied to a 0.7% agarose gel for electrophoresis. The rate of migration of the mixture of the two DNA orientations was found to be slower than it was when each DNA sample was incubated separately at 67° C. This slower rate of migration indicated that the two DNA samples were complementary to one another, confirming that the samples contained vectors with opposite orientation DNA.

Step 3. Characterization of the Cloned Molecules Containing The 4.5 kb EcoRI DNA Segment Cloned DNA molecules which had the 4.5 kb EcoRI segment inserted in both orientations were selected using the methods described in Step 2.

Since it is possible that the cloning procedure itself can introduce rearrangements in the nucleotides of the DNA sequence making subsequent DNA sequencing meaningless, a final check was made. Specifically, as a final check on the orientation and identity of the molecules containing the 4.5 kilobase EcoRI segment, approximately 200 nucleotides of the 4.5 kb EcoRI target DNA segment adjacent to the sequencing primer binding site were determined (using the dideoxy chain termination method as described by Sanger PNAS, supra, 1977) on vectors containing both orientations of the EcoRI segment. This confirmed that one recombinant contained DNA overlapping about 400 basepairs of previously sequenced DNA [Henikoff et al., supra (1983)] so that the remaining approximately 4 kb corresponds to the previously unsequenced 5' portion of the Gart locus. Further confirmation was obtained by Southern blot analysis, which involves a filter paper method for detecting DNA fragments that are complementary to a given DNA sequence [Southern, Methods in Enzymology 68:152 (1979)]. This analysis was used and verified that the 4.5 kb EcoRI target DNA segment present in each of the two recombinants was also present in the Drosphila genome. Both recombinants were then processed in the manner described below.

Step 4. Preparation of Cloned Molecules, Shortening of the 4.5 kb Double-Stranded EcoRI Target DNA Segment Each of the two recombinant bacteriophage clones characterized in Step 3, above, was used to infect *E. coli* cells to isolate the corresponding double-stranded replicative form (RF) DNA. The RF was obtained by first harvesting 300 ml of the cultures by centrifugation of the cells at 5000 Xg and 4° C., discarding the supernatant. The cells were lysed using the method of Ish-Horowicz and Burke [Nucl. Acids Res. 9,2989 (1981)] and the double-stranded circular DNA molecules were purified using the well-known method of cesium chloride gradient centrifugation.

(a) Cleavage by two restriction endonucleases

The samples containing the two different orientations of the target DNA segments were cleaved with a variety of restriction endonucleases to determine which endonucleases would cleave at unique sites within the polylinker region between the EcoRI insertion site and the oligonucleotide primer binding site and which fail to cleave at sites in the 4.5 kb inserted target DNA segment and, thus, yield full size linear DNA molecules for both insert orientations. It was found that Sal I, which leaves a four base, 5' protrusion, and SphI, which leaves a four base, 3' protrusion (See FIG. 2), met the foregoing requirements. These enzymes, obtained from New England Biolabs, were used to completely digest 5–10 ug of the samples containing the two oppositely oriented target DNA segments in the manner recommended by the manufacturer. The DNA was then ethanol precipitated and one of the two samples treated as described below.

(b) Progressive Unidirectional Digestion of the EcoRI Target DNA Segment by Exonuclease III The DNA pellets that resulted from the enzymatic cleavage of the samples as described above (Step 4a) were then dissolved in 66 mM Tris-HCl [pH 8], 0.66 mM MgCl$_2$ to a concentration of approximately 100 ug/ml. One-tenth volume of *E. coli* Exonuclease III (obtained from Bethesda Research Labs, 67,000 units/ml) was added to the solution to give a molar excess of enzyme over DNA molecules, which was calculated to be about twenty to one.

The reaction tube was mixed and equilibrated to 37° C. as rapidly as possible. Aliquots of 2.5 μl were removed at 35 second intervals and mixed with 7.5 μl 0.2 N Nacl, 5mM EDTA [pH 8] in 0.5 ml microfuge tubes which stopped the reaction. After each sample had been removed the exonuclease was permanently inactivated by incubation at 70° C. for 10 minutes. The DNA was then precipitated by addition of 30 μl of ethanol to each sample, chilled to −70° C., and pelleted by centrifugation at 8000 G at 22° C., in an Eppendorf microfuge for 5 minutes. The pellet was then rinsed with 100 μl ethanol, decanted and dried.

(c) SI Nuclease Treatment of Exonuclease III Digested DNA Molecules

Each pellet formed during Step 4(b) was dissolved in 50 μl 0.25M NaCl, 30 mM potassium acetate [pH 4.6], 1mM ZnS0$_4$, 5% glycerol and 67 Vogt units/ml S1 nuclease (obtained from Bochringer Mannheim Biochemicals, 941 Castleway Drive, P.O. Box 50816, Indianapolis, IN 46250) and incubated for 30 minutes at 22° C. to remove the single strands generated by exonuclease III digestion. The reactions were stopped by addition of 6 μl of 0.5M Tris [pH 8], 0.125M EDTA. Portions of selected 20 μl aliquots were examined by electrophoresis on 0.7% agarose gel to determine the actual rate of exonuclease III degradation and to decide which aliquots would be used based on the extent of digestion. This analysis revealed that the 19th aliquot of aliquots removed at 35 second intervals contained no target DNA, based on the rate of migration of the sample in the agarose gel. Therefore, the first 18 aliquots were processed further, while all subsequent aliquots, representing deleted molecules with no remaining target DNA, were discarded. Samples were vortexed briefly with 25 μl phenol and then with 25 μl chloroform, spun in a microfuge 8000 Xg at 22° C. and the aqueous layers transferred to fresh 0.5 ml tubes. After addition of 140 μl of ethanol, the samples were chilled. The DNA was then pelleted, precipitated, rinsed and dried.

(d) Circularization of Linear DNA Molecules

Each DNA pellet produced in Step 4(c), which corresponded to an exonuclease digestion time point, was dissolved in 10 μl 20 mM Tris-HCl [pH 8], 7 mM MgCl$_2$ and 10 units/ml large fragment (Klenow) DNA polymerase I (obtained from New England Nuclear, 549 Albany St., Boston, MA 02118) and incubated for approximately 2 minutes at 37° C. A 1 μl volume of a mixture of the four deoxynucleotide triphosphates (dNTPs) (obtained from Pharmacia PL Biochemicals, Inc., 2202 Ninth Bartlett Ave., Milwaukee, WI 53202), each at a concentration of 0.125 mM was added and the mixture incubated at 37° C., for approximately 2 minutes longer. This procedure efficiently removed both 5' and 3' nucleotide protrusions, leaving ligatable blunt ends for insertion into an appropriate cloning vehicle [Henikoff, Nucl. Acids Res. 11, 4735 (1983)].

Each sample was then mixed at room temperature with 40 μl 66 mM Tris-HCl [pH 7.6], 6.6 mM MgCl$_2$, 10 mM dithiothreitol, 100 ug/ml bovine serum albumen, 1 mM spermidine, 0.2 mM ATP and 25 units/ml T4 DNA ligase (obtained from New England Biolabs) to ligate the deleted linear EcoRI DNA molecules thus reforming circular M13 mp18 DNA molecules. After several hours at room temperature, to facilitate DNA uptake by the cells, 20 μl of each sample was added to 100 μl *E. coli* 71-18 cells that had been previously treated with 50 mM CaCl$_2$ by standard methods to facilitate DNA uptake by the cells and stored frozen in 50 mM CaCl$_2$, 15% glycerol at −70° C. The transfected cells were then plated using standard techniques, obtaining approximately 200–2000 plaques per sample [See Messing, supra (1983)]. Next, individual plaques formed on the plates were selected. First, the smallest plaques from the plates, which corresponded to the first few aliquots, were selected. Gradually, the size of the plaques chosen from subsequent plates was increased. These plaques were used to infect 1.5 ml cultures of E.coli strain 71-18 and grown for twelve hours for the preparation of single-stranded bacteriophage DNA.

After centrifugation at 8000 Xg for 5 minutes at 22° C. to remove the cells, the bacteriophage containing single-stranded DNA were precipitated from the medium using polyethylene glycol (PEG) 6000. The precipitated single-stranded phage were dissolved at 55° C. in 50 μl of 10 mM Tris-HCl [pH 8], 1 mM EDTA, 0.2% Sarkosyl, 50 ug/ml proteinase K, then extracted with phenol, chloroform and ether. The DNA was precipitated with ethanol and dissolved in 50 μl of 10 mM Tris-HCl [pH 7.8], 1 mM EDTA. This treatment results in cloned single-stranded circular recombinant DNA molecules.

(e) Sequencing of Cloned, Circular DNA Molecules Containing EcoRI DNA Molecules (1) T-track analysis The cloned circular DNA molecules produced when the preceeding steps were followed were segregated so that the expected sizes of the shortened target DNA segments differed by an amount of DNA small enough (approximately 200–250 bases) to allow completed DNA sequence determination, without further subdivision. The selected samples were then characterized by T-track analysis using buffer gradient electrophoretic gels [Biggin, Gibson, Hong, PNAS USA 80:3963 (1983)], which allowed comparisons to be made for more than 300 bp of DNA run in each gel lane.

A total of 135 cloned DNA molecules from the 18 plates derived by plating successive aliquots used in this example were characterized by T-track, or complete dideoxynucleotide triphosphate chain termination analysis (discussed below).

(f) Complete Sequence Analysis

Complete sequence analysis was done on 26 cloned DNA molecules spanning the 4.5 kb region of the *Drosophila melanogaster* DNA fragment. This was done using the Sanger dideoxynucleotide triphosphate (ddNTP) chain termination method of sequencing (Sanger, supra 1977).

Each deletion breakpoint in the group of cloned DNA molecules containing shortened versions of the original 4.5 kb EcoRI DNA segment was separated from the next deletion breakpoint by an interval of no more than 250 bp. Thus, the entire sequence for one strand of the original EcoRI DNA segment was determined with a single sequencing reaction on each clone on a buffer gradient gel. The gel was read and the information stored with the aid of a computer. Running of successive derivative deleted molecules in adjacent sets of gel lanes facilitated this process. The completed sequence was proofread twice by direct comparison to the autoradiograms.

(g) Verification of the First Example Data by Complete Sequencing of the Complementary Strand of the Cloned EcoRI DNA Segment To verify the data obtained in (f) above, the sequence of the other strand of the 4.5 kb EcoRI fragment was determined by applying the above procedure to the 4.5 kb EcoRI segment carried in the opposite orientation in the M13 ffmp18 vector. The complete sequence file that resulted was proofread twice by direct comparison to the autoradiograms. Verification and correction of data was accomplished by comparison of the data for both DNA strands followed by references to the appropriate gel regions on the original autoradiograms to resolve any discrepancies. This procedure essentially assures 100% reliability of the final sequence.

Figure 4B:
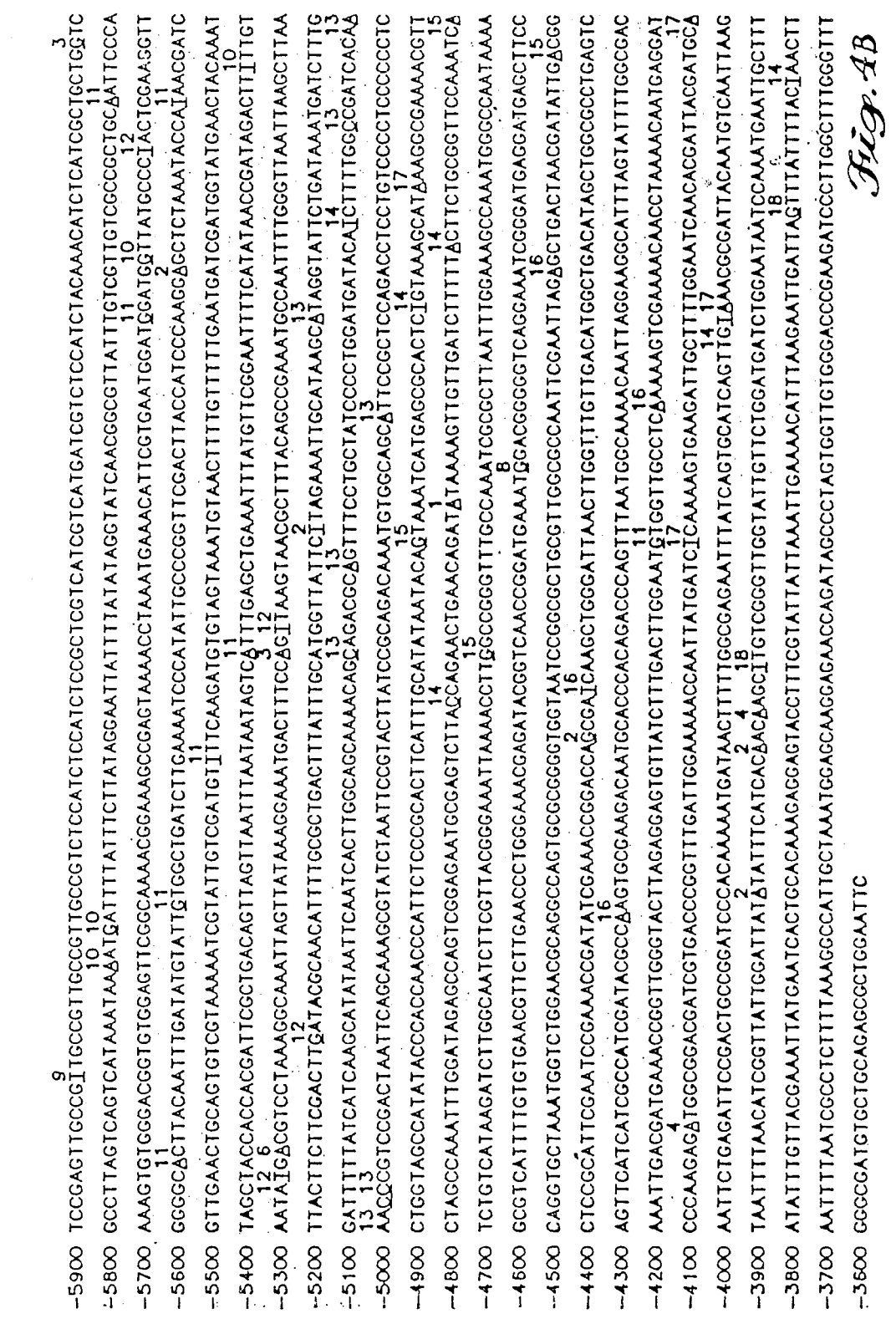

(h) Result of the Sequencing of the 4.5 kb EcoRI DNA Segment of Drosophila melanogaster The results of applying the instant process to the 4.5 kb EcoRI DNA segment are depicted in FIGS. 3, 4A and 4B.

FIG. 3 is a graph that shows the distribution of shortened target DNA segments (kilobases deleted) as a function of exonuclease III reaction time. The diagonal line represents a uniform exonuclease digestion rate of 450 bases per minute, after a 25 second delay. The close correspondence of most breakpoints to this line and the clustering of deletions at each digestion timepoint demonstrates that the synchrony of exonuclease digestion is adequate for targeting deletions relatively distant from a starting point at one end of a target DNA segment. The resulting clones derived from each exonuclease III timepoint are shortened (deleted) to a predicted extent with only slight scatter, even over regions 4,000 bp and longer. In all, 85% of the clones characterized were deletions that could be used for sequence analysis and, of these, about 70% were deleted to the extent expected on the basis of exonuclease digestion time.

FIGS. 4A and B show the same data from FIG. 3 superimposed on the final DNA sequence, according to the precise location of the deletions that occurred within the EcoRI segment. Each deletion is identified by the Exonuclease III aliquot number where 1 was digested for 35 seconds, 2 for 70 seconds . . . up to 18 for 630 seconds. No sequence preference is seen which is consistent with the uniformity of exonuclease III movement at 37° C. implicit in FIG. 3. Thus, the method described here allows for targeting of the deletions in virtually any DNA segment that can be cloned into an appropriate vector.

EXAMPLE II

Demonstration of Synchronous Action and Selectivity of Exonuclease III

Bacteriophage lambda DNA (obtained from Bethesda Research Laboratories), was digested with the restriction endonuclease SstI (obtained from New England Biolabs), an enzyme that cleaves twice very near the midpoint of the 48 kilobase DNA molecule leaving four nucleotide protrusions at the 3' end of the molecule (FIG. 5). Conditions for digestion were those recommended by the manufacturer. Two large double-stranded pieces of DNA (24.8 kb and 22.6 kb) with 5', 12 nucleotide protrusions at one end and one short 1.1 kb piece of DNA with 3' four nucleotide protrusions at both ends resulted from this cleavage. When these pieces were digested by exonuclease III (under the conditions described in Example I) the two large pieces were digested from the 5' protrusion end, but not from the Sst I generated (3' protruding) ends. The internal 1.1 kb fragment with 3' protrusions was not digested.

The digestion products from this reaction were electrophoresed on a 0.55% agarose gel after aliquots had been removed at 4 minute intervals from the exonuclease III digestion mixture and treated with S1 nuclease as described above in Example I, prior to loading on the gel. The gel demonstrated the synchronous digestion by exonuclease III since the two large terminal DNA fragments continued to be visible as sharp bands even after 32 minutes of digestion at 37° C., when 14.4 kb of DNA sequence had been removed from each 5' protruding end. However, no change in the size or amount of the internal 1.1 kb fragment was seen which indicated that the SstI 3' protruding ends were not detectably digested by the enzyme exonuclease III.

The above data can be used to calculate a rate of digestion of 450 nucleotide bases per minute for the enzyme at 37° C. under the conditions used. There was a DNA "smear" in the gel lanes, apparently a by-product of the S1 nuclease digestion which appeared to cause an average of about one double-stranded break for every 20 kb under the noted conditions.

As will be appreciated by those skilled in the art and others from the foregoing description, this invention provides time-saving advantages by eliminating steps associated with the preparing of the DNA molecules derived from target DNA segments for sequencing and, thus, facilitates the sequencing of relatively long pieces of DNA. Previously, long segments were most easily determined using relatively complex computer assistance for ordering the fragments chosen at random after restriction endonuclease cleavage of the original DNA segment or by random fragmentation of the DNA segment. Additionally, this invention provides a method for targeting of a particular region within a long target DNA segment for whatever molecular manipulation the user wishes. The user can perform the sequencing on a given long target DNA segment and, then, single out a particular region for subsequent manipulation; the region selected corresponds to the intervals between deletion breakpoints as calculated from exonuclease digestion time.

While preferred embodiments of the invention have been illustrated and described, it is to be understood that, within the scope of the appended claims, various changes can be made therein. Hence, the invention can be practiced in ways other than those specifically described herein.

The embodiments of the invention in which an exclusive property or privilege is claimed are defined as follows:

1. A process for producing a plurality of cloned, circular DNA molecules containing shortened target DNA fragments, said fragments derived from a long target DNA segment, said cloned, circular DNA molecules suitable for use in determining the nucleotide sequence of said long target DNA segment, comprising the steps of:

producing, by molecular cloning, a plurality of double-stranded circular recombinant DNA molecules, each molecule containing vector DNA, a sequencing primer binding site, and a DNA region comprising a long target DNA segment, a first restriction site adjacent to said long target DNA segment adapted to be cut by a first restriction endonuclease in a manner that creates a first terminus on the DNA molecules adjacent the long target DNA segment that is susceptible to digestion by an exonuclease, and a second restriction site located between said first restriction site and said sequencing primer binding site adapted to be cut by a second restriction endonuclease in a manner that creates, without additional terminus blocking or digestion, a second terminus on the DNA molecules that is not susceptible to digestion by an exonuclease;

cutting said double-stranded circular recombinant DNA molecules at said first restriction site using a first restriction endonuclease and at said second restriction site using a second restriction endonuclease to form double-stranded linear recombinant DNA molecules having a first terminus that is susceptible to digestion by an exonuclease and a second terminus that is not susceptible to digestion by an exonuclease;

unidirectionally digesting the linear double-stranded DNA molecules with an exonuclease from the first terminus that is susceptible to digestion by an exonuclease, without digesting vector DNA contained in the linear double stranded DNA molecules;

removing, at timed intervals during the unidirectional digestion, a portion of the exonuclease digested linear double-stranded DNA molecules;

circularizing the shortened linear DNA molecules; and cloning the circular DNA molecules and isolating the clones to obtain a plurality of circular DNA molecules containing overlapping target DNA fragments derived from the long target DNA segment.

2. The process according to claim 1, wherein said exonuclease is characterized by its ability to unidirectionally digest nucleotide bases at a substantially uniform and synchronous rate over up to 14kb or more nucleotides of target DNA.

3. The process according to claim 2 wherein said exonuclease is Exonuclease III.

4. The process according to claim 1, wherein said step of unidirectionally digesting from said terminus that is susceptible to digestion comprises removing nucleotides at a substantially uniform and synchronous rate from the end of the target DNA segment nearest to said susceptible terminus.

5. The process according to claim 1 wherein said process further comprises the step of selecting cloned recircularized DNA molecules containing shortened, overlapping target DNA fragments suitable for sequencing.

6. The process according to claim 5 wherein said step of selecting cloned DNA molecules suitable for sequencing comprises selecting clones which correspond to a predetermined time of unidirectional digestion by an exonuclease.

7. The process according to claim 6 wherein said step of selecting cloned DNA molecules suitable for sequencing comprises selecting those clones carrying shortened, overlapping target DNA fragments which differ by approximately 200 nucleotides or less in length.

8. The process according to claim 6 wherein said determination time of unidirectional digestion is selected to correspond to that which is required to digest a preselected region of DNA.

9. The process according to claim 8 wherein said preselected region of DNA is a gene of interest.

10. The processing according to claim 1 wherein said exonuclease is *E. coli* exonuclease III.

11. The process claimed in claim 1 wherein said plurality of double-stranded circular recombinant DNA molecules each containing: (i) vector DNA; (ii) a sequencing primer binding site; and, (iii) a DNA region having unique restriction endonuclease sites and a long target DNA segment are filamentous bacteriophage DNA molecules.

12. The process claimed in claim 11 wherein said double-stranded filamentous bacteriophage molecules into which said long target DNA segment is inserted are M13 filamentous bacteriophage DNA molecules isolated from *E. coli* bacterial cells.

13. The process claimed in claim 12 wherein said M13 filamentous bacteriophage DNA molecules isolated from *E. coli* bacterial cells are M13 mp18 vectors.

14. The process claimed in claim 12 wherein said M13 filamentous bacteriophage DNA molecules isolated from *E. coli* bacterial cells are M13 mp19 vectors.

15. The process according to claim 1 wherein the recombinant DNA molecules include target DNA inserted in both orientations.

16. The process according to claim 15 wherein said plurality of double-stranded recombinant DNA molecules are filamentous bacteriophage DNA molecules.

17. The process claimed in claim 16 wherein the filamentous bacteriophage DNA molecules are converted into a plurality of double-stranded recombinant filamentous bacteriophage DNA molecules by a process comprising: infecting host cells with said double-stranded filamentous bacteriophage DNA molecules to create a plurality of phage particle containing single-stranded recombinant bacteriophage DNA molecules, some of one target DNA orientation, and others of the opposite target DNA orientation; selecting single-stranded recombinant bacteriophage DNA molecules of one target DNA orientation from said plurality of phage particles; and, transfecting a suitable cell culture with said selected single-stranded recombinant bacteriophage DNA molecules to create said plurality of double-stranded recombinant filamentous bacteriophage DNA molecules each containing: (i) vector DNA; (ii) a sequencing primer binding site; and (iii) a DNA region having unique restriction endonuclease sites and a long target DNA segment.

18. The process claimed in claim 1, wherein said first restriction endonuclease cuts said double-stranded recombinant DNA molecules by cleaving said double-stranded recombinant DNA molecules such that said terminus has a 5' protrusion that is susceptible to digestion by an exonuclease.

19. The process claimed in claim 18 wherein said second restriction endonuclease cuts said double-stranded recombinant DNA molecules by cleaving said double-stranded DNA molecules such that said terminus has a 3' protrusion of at least four nucleotides that is not susceptible to digestion by an exonuclease.

20. The process according to claim 19 wherein said exonuclease is *E. coli* Exonuclease III.

21. The process according to claim 19 wherein said double-stranded recombinant DNA molecules each containing: (i) vector DNA, (ii) a sequencing primer binding site; and (iii) a DNA region having unique restriction endonuclease sites and a long target DNA segment are filamentous bacteriophage DNA molecules.

22. The process claimed in claim 21 wherein said double-stranded filamentous bacteriophage molecules into which said long target DNA segment is inserted are M13 filamentous bacteriophage DNA molecules isolated from *E. coli* bacterial cells.

23. The process claimed in claim 22 wherein said M13 filamentous bacteriophage DNA molecules isolated from *E. coli* bacterial cells are M13 mp18 vectors.

24. The process claimed in claim 22 wherein said M13 filamentous bacteriophage DNA molecules isolated from *E. coli* bacterial cell are M13 mp19 vectors.

25. The process claimed in claim 1 wherein the step of creating a plurality of circular DNA molecules containing overlapping target DNA fragments derived from said long DNA segment includes the substep of removing remaining single-stranded nucleotides from said DNA fragments after they are removed during said unidirectional digestion, prior to being circularized, by applying a single-stranded specific nuclease to said deleted DNA fragments.

26. The process claimed in claim 25 wherein said single-stranded specific nuclease used in said substep of removing remaining single-stranded nucleotides from said DNA fragments after they are removed during said unidirectional digestion is Aspergillus oryzea S1 nuclease.

27. The process according to claim 25 wherein said exonuclease is *E. coli* Exonuclease III.

28. The processing according to claim 27 wherein said double-stranded circular recombinant DNA molecules each containing: (i) vector DNA, (ii) a sequencing primer binding site; and, (iii) a DNA region having unique restriction endonuclease sites and a long target DNA segment are filamentous bacteriophage DNA molecules.

29. The process claimed in claim 28 wherein said double-stranded filamentous bacteriophage molecules are M13 filamentous bacteriophage DNA molecules isolated from *E. coli* bacterial cells.

30. The process claimed in claim 29 wherein said M13 filamentous bacteriophage DNA molecules isolated from *E. coli* bacterial cells are M13 mp~ vectors.

31. The process claimed in claim 29 wherein said M13 filamentous baceriophage DNA molecules isolated from and *E. coli* bacterial cell are M13 mp19 vectors.

32. The process claimed in claim 1, wherein said substep of circularizing said deleting DNA fragments to reform double-stranded DNA molecules comprises removing protrusion from the termini of said fragment using Klenow polymerase and ligating said deleted DNA fragments using T4 DNA ligase.

33. The process according to claim 32 wherein said exonuclease is *E. coli* exonuclease III.

* * * * *

UNITED STATES PATENT AND TRADEMARK OFFICE
CERTIFICATE OF CORRECTION

PATENT NO. : 4,843,003

DATED : June 27, 1989

INVENTOR(S) : Henikoff et al.

It is certified that error appears in the above-identified patent and that said Letters Patent is hereby corrected as shown below:

On the title page:

Section [57], line 24: "DNa" should be --DNA--

Section [57], line 35: "recirculated" should be --recircularized--

Section [56], fourth reference: "Targetted" should be --Targeted--

Section [56], fifth reference: "Phosphosothroate" should be --Phosphurothroate--

Section [56], fifth reference: "Replocated" should be --Replicated--

Column 1, line 18: "polya crylamide" should be --polyacrylamide--

Column 1, line 20: after "up" delete "to"

Column 5, line 2: "created" should be --create--

Column 6, line 61: "in vivo" should be --in vivo--

Column 7, line 10: "organism" should be --organisms--

Column 7, line 40: "endonuclease" should be --endonucleases--

Column 7, line 50: after "5' " (first occurrence) insert --direction--

Column 7, line 50: "protuding" should be --protruding--

Column 9, line 20: "in vitro" should be --in vitro--

Column 9, line 66: "β-galatosidase" should be --β-galactosidase--

Column 10, line 2: "sites," should be --sites--

Column 10, line 4: "other.)" should be --other).--

Column 11, line 33: "IIR" should be --RRI--

Column 12, line 60: "protusion" should be --protrusion--

Column 13, line 63: "exonucleases" should be --exonuclease--

UNITED STATES PATENT AND TRADEMARK OFFICE
CERTIFICATE OF CORRECTION

PATENT NO. : 4,843,003

DATED : June 27, 1989

INVENTOR(S) : Henikoff et al.

It is certified that error appears in the above-identified patent and that said Letters Patent is hereby corrected as shown below:

Column 15, line 30: "protusion" should be --protrusion--

Column 17, line 19: "Charon4" should be --Charon-4--

Column 17, line 22: "(1983)." should be --(1983)].--

Column 18, line 46: "Drosphila" should be --Drosophila--

Column 20, line 53: "completed" should be --complete--

Column 21, line 25: "ffmp18" should be --mp18--

Column 22, line 48: after "of" delete "the"

Column 23, lines 3-5: "The embodiments of the invention ... as follows:" should be
 --What is claimed is:--

Claim 8, line 2: "determination" should be --predetermined--

Claim 17, line 7: "particle" should be --particles--

Claim 25, line 8: "single-stranded" should be --single-strand--

Claim 26, line 2: "single-stranded" should be --single-strand--

Claim 30, line 3: "mp-" should be --mp18--

Claim 31, line 3: "and" should be --an--

Claim 32, line 2: "deleting" should be --deleted--

UNITED STATES PATENT AND TRADEMARK OFFICE
CERTIFICATE OF CORRECTION

PATENT NO. : 4,843,003
DATED : June 27, 1989
INVENTOR(S) : Henikoff et al.

It is certified that error appears in the above-identified patent and that said Letters Patent is hereby corrected as shown below:

Claim 32, line 4: "protrusion" should be --protrusions--

Signed and Sealed this

Fifteenth Day of January, 1991

Attest:

HARRY F. MANBECK, JR.

*Attesting Officer*     *Commissioner of Patents and Trademarks*